US012589178B2

(12) United States Patent　　　(10) Patent No.:　US 12,589,178 B2
Sümegi et al.　　　　　　　　　　　(45) Date of Patent:　　Mar. 31, 2026

(54) AIR STERILISATION APPARATUS

(71) Applicants:István Andor Sümegi, Dunakeszi
(HU); Ágnes Sipos, Dunakeszi (HU)

(72) Inventors: István Andor Sümegi, Dunakeszi
(HU); Ágnes Sipos, Dunakeszi (HU)

( * ) Notice: Subject to any disclaimer, the term of this
patent is extended or adjusted under 35
U.S.C. 154(b) by 562 days.

(21) Appl. No.: 18/265,532

(22) PCT Filed: Dec. 7, 2021

(86) PCT No.: PCT/HU2021/050068
§ 371 (c)(1),
(2) Date: Jun. 6, 2023

(87) PCT Pub. No.: WO2022/123277
PCT Pub. Date: Jun. 16, 2022

(65) Prior Publication Data
US 2024/0024529 A1　　　Jan. 25, 2024

(30) Foreign Application Priority Data

Dec. 7, 2020　　(HU) .............................. HU/P2000413
Jun. 8, 2021　　(HU) ............................. HU/P2100218

(51) Int. Cl.
A61L 9/16　　　　　(2006.01)
F24F 8/20　　　　　(2021.01)
(Continued)

(52) U.S. Cl.
CPC .............. A61L 9/16 (2013.01); F24F 12/006
(2013.01); *A61L 2209/111* (2013.01);
(Continued)

(58) Field of Classification Search
CPC .... A61L 9/16; A61L 2209/10; A61L 2209/11;
A61L 2209/111; A61L 2209/14;
(Continued)

(56) References Cited

FOREIGN PATENT DOCUMENTS

CN　　　2655086　Y　*　11/2004
CN　　　1608680　A　*　4/2005
(Continued)

OTHER PUBLICATIONS

Machine translation of CN 102698297B (Year: 2014).*
(Continued)

*Primary Examiner* — Robert Clemente
(74) *Attorney, Agent, or Firm* — Daniel S. Kim

(57)　　　　　　ABSTRACT

The air sterilizer comprises a housing (1), at one end of
which there is an air inlet unit (5) in which a fan (3) is
arranged in a fixed manner; a spiral plate heat exchanger (2)
arranged in the housing (1), in the center of which an electric
heating unit (7) is arranged; an air outlet unit (6) at the other
end of the housing (1); wherein the spiral plate heat
exchanger (2) has an air inlet duct (31) running from the air
inlet unit (5) to the electric heater (7) and a counterflow air
outlet duct (32) running from the electric heater (7) to the air
outlet unit (6), which ducts (31, 32) run helically next to
each other. At one end of the housing (1) of the air sterilizer,
adjacent to the air inlet unit (5), an air outlet (18) is formed
on each side of the housing (1). Each side of the spiral plate
heat exchanger (2) is sealed by an end cover. An air inlet (19)
is formed on the end covers, which opens into the air inlet
duct (31) running to the electric heating unit (7). A guide
hole is formed in the end cover for a temperature sensor in
which a temperature sensor is accommodated. In the spiral
plate heat exchanger (2), there is a constant distance between
the plates forming the air inlet duct (31) and the air outlet
duct (32). The end covers have a heat-insulated side cover on
each side of the air sterilizer, which side covers are sealed to
the housing (1) and define a respective chamber which
establishes flow communication between the air outlet and
the air inlet on the same side of the air sterilizer.

10 Claims, 16 Drawing Sheets

(51) Int. Cl.
    *F24F 12/00*      (2006.01)
    *F28D 9/04*       (2006.01)
    *F28D 21/00*     (2006.01)

(52) U.S. Cl.
    CPC ....... *A61L 2209/14* (2013.01); *A61L 2209/15*
        (2013.01); *F24F 8/20* (2021.01); *F28D 9/04*
            (2013.01); *F28D 21/0008* (2013.01)

(58) Field of Classification Search
    CPC ....... A61L 2209/15; F24F 12/006; F24F 8/20;
          F24F 8/80; F28D 9/04; F28D 21/0008
    See application file for complete search history.

(56)               References Cited

FOREIGN PATENT DOCUMENTS

| CN | 102698297 | B | * | 10/2014 |
| JP | 2004236896 | A | * | 8/2004 |

OTHER PUBLICATIONS

Machine translation of CN 1608680A (Year: 2005).*
Machine translation of CN2655086Y (Year: 2004).*
English abstract of JP2004236896A (Year: 2004).*

* cited by examiner

AIR STERILISATION APPARATUS

This is the national stage of International Application PCT/HU2021/050068, filed Dec. 7, 2021.

The present invention relates to an air sterilizer, in particular to an air sterilizer comprising a spiral plate heat exchanger having an air inlet duct from an air inlet unit to a central electric heating unit and a counter-current air outlet duct from the electric heater unit to an air outlet unit, said ducts running helically next to each other.

The fight against Covid 19 coronavirus is a major challenge for humanity today, from the point of view of both health and economy. People are dying, human destinies are being ruined by its devastating negative effects on health and the economy. Therefore, any solution, idea, or invention can be vital in any field of art that can prevent the spread of the virus and the infections, and can promote effective control at both individual and societal levels.

Various solutions for air sterilizers are known in the art. Such a device is described, for example, in the patent application HU P0400912. Said document discloses, inter alia, an air purification device that sprays water through a nozzle onto a metal sheet. The voltage applied to the nozzle and thus to the water attracts the contaminants in the air, so they bind to the water and follow it as it flows into a collecting basin, which then transports the contaminated water to the sewer system of the building.

Another solution is to use germicidal lamps that emit UV radiation, which emit UV radiation in the wavelength range of 200-300 nm, which is effective in killing airborne bacteria and viruses.

Other solutions include fan-operated air purifiers, which purify the air by various filters and thus filters out pathogens and viruses.

Other solutions also include the heat sterilizers (chambers) used in healthcare to sterilize medical devices.

Further solutions are the photocatalytic air purifiers, which produce hydroxyl radicals and free radicals and thus destroy viruses and other pathogens in the air.

Another solution is disclosed in the document WO 2020/197143 A1, which thermally decomposes odours and odour components generated during the treatment of food waste, animal husbandry, composting and fermentation of agricultural waste by means of heat, wherein the air flow is provided by a fan, the heated air is cooled to a temperature that complies with environmental regulations by means of a heat exchanger. The equipment is designed for industrial use.

The disadvantage of the above described solutions is that the voltage-treated water spray does not attract viruses from the air and the device is difficult to mobilize, and its installation requires the existence of a water supply system and sewerage system.

The disadvantage of the germicidal lamps that emit UV radiation is that their radiation is dangerous to humans, animals and plants, so it should only be used when there are no living things nearby. Its reaction time is slow, several minutes of irradiation is required to kill the viruses.

A serious disadvantage of the fan-type air purifiers with filters is that they do not destroy the airborne pathogens and viruses, but collect them in their filters, so they remain active and infectious, and thereby during their operation, infectious foci may form in the filters with which we are in a common airspace. It is only a matter of time before their filter system saturates with virus and re-infects the cleaned air. Therefore, the filters need to be replaced frequently, which is a significant cost. Another disadvantage is that improper replacement and storage of filters can easily cause serious infection.

The disadvantage of the heat sterilizers (chambers) is that the infected tools must be treated with hot dry air at a temperature of 160-200° C. for 10-45 minutes. These devices are not suitable for immediate control of airborne viruses. Because of their design, neither are they suitable for exchanging air and disinfecting it.

The disadvantage of the photocatalytic air purifiers is that they use hydroxyl (HO) free radicals to purify the air, which are highly reactive aggressive molecules, and the free radicals in the air can be inhaled directly during operation. It is well known that free radicals are also largely responsible for the aging of the human body. It is advisable to keep contact with them to a minimum. Another disadvantage is that the prices of these devices are very high.

The disadvantage of the deodorizing device disclosed in WO 2020/197143 A1 is that its structural design, the design, the layout and the operation concept of the heating system of its heat exchanger have been developed for industrial use for the purpose of neutralizing the odours releasing at fermenting and composting decomposing food waste, waste from animal husbandry and agricultural waste, as well as the odours from wastewater treatment, and it does not provide adequate protection against airborne pathogens, especially viruses.

The aim of the solution according to the invention was to provide an antiviral air exchange apparatus based on new innovative solutions responding to the recent challenges, and which eliminates the above-mentioned problems and shortcomings, offers a complex solution for the protection against coronavirus and other viruses, and which, in daily use in the immediate vicinity of humans and living things, can be used continuously in practice, without harming or endangering their health.

The invention is based on the idea that the air sucked in by the apparatus, infected with coronavirus or other viruses, is sterilized in a reaction chamber centrally located inside a spiral plate heat exchanger of the apparatus in such a way that the air having a temperature in the range of 310-600° C. within the reaction chamber immediately destroys the viruses. The sterilized hot air, which has been cooled back (approximately to the intake air temperature), is then blown back into the environment so that there is a side cover on each side of the spiral plate heat exchanger, which side covers provide flow communication between the air outlet and the air inlet arranged on the same side of the apparatus. Thus, the sides of the spiral plate heat exchanger are also continuously cooled, and the heated air generated there is returned to the spiral plate heat exchanger system. Thanks to this solution, favourable energy-saving operation is achieved, and despite the high internal operating temperature (310-600° C.), the external parts and covers of the apparatus do not heat up, which is of key importance for practical applicability. With the continuous use of the device, virus-free, healthy air is delivered into the treated room, the microenvironment and the overall environment.

The objects are achieved by providing an air sterilizer which comprises a housing having an air inlet unit at one end in which a fan is mounted in a fixed manner, a spiral plate heat exchanger arranged in the housing and having an electric heating unit in the center thereof, an air outlet unit at the other end of the housing, wherein the spiral plate heat exchanger has an air inlet duct from the air inlet unit to the electric heating unit and a counter-current air outlet duct from the electric heater unit to the air outlet unit, the ducts running helically next to each other.

At one end of the housing of the apparatus, near the air inlet unit, there is an air outlet on each side of the housing of the apparatus. Each side of the spiral plate heat exchanger is sealed by an end cover, the end covers being provided with an air inlet opening into the air inlet duct leading to the electric heating unit. A guide hole for a temperature sensor is formed in the end cover in which a temperature sensor is located. In the spiral plate heat exchanger, there is a constant distance between the plates forming the air inlet ducts and the air outlet ducts. The end covers have a heat-insulated side cover on each side of the apparatus, which is tightly connected to the housing of the apparatus, and wherein each of the side covers defines a chamber which establishes flow communication between the air outlet and the air inlet on the same side of the apparatus.

The air sterilizer according to the invention will now be described in more detail with reference to the accompanying drawings.

Figure 1:
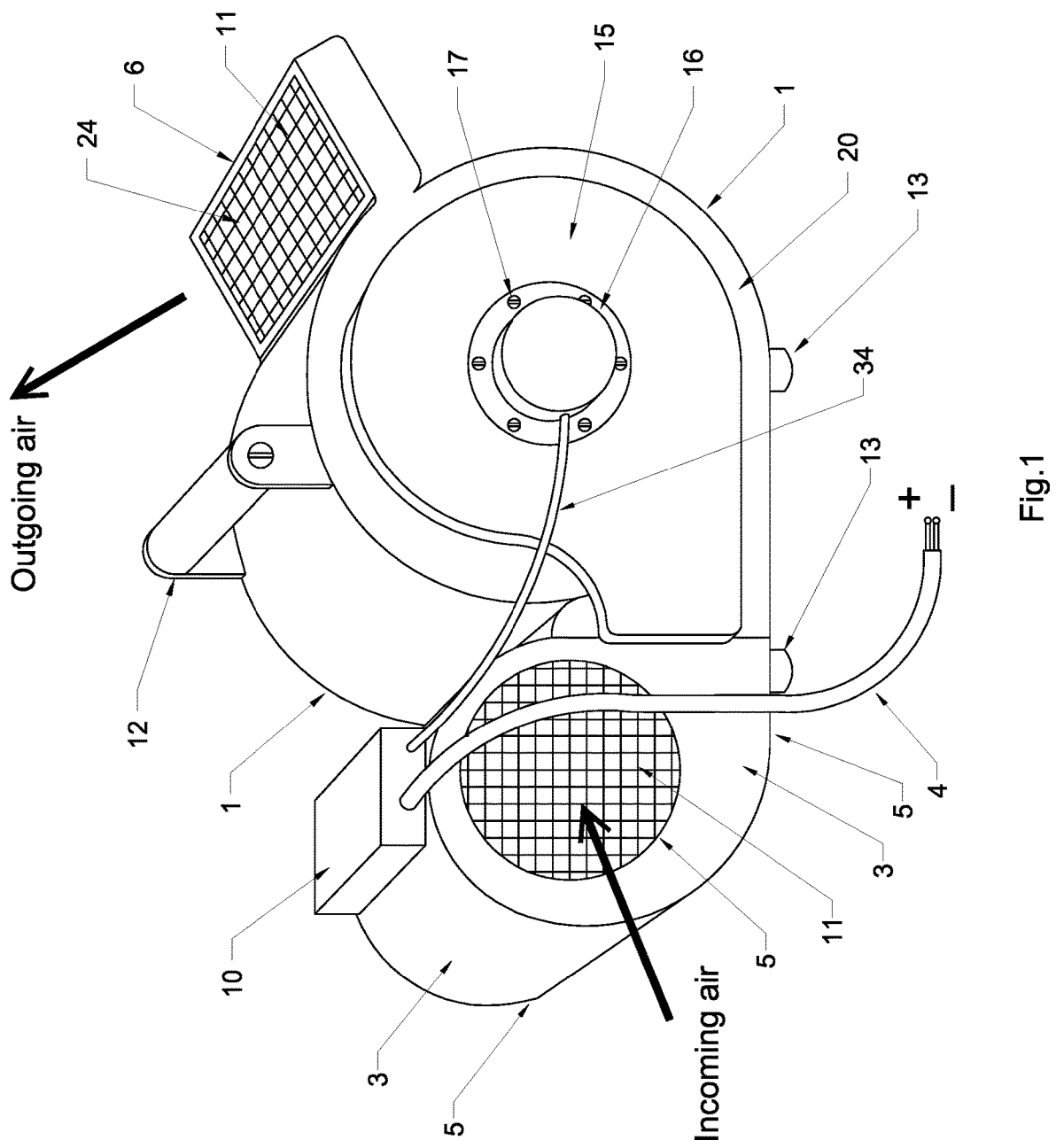
FIG. 1 shows a perspective view from a right side of an embodiment of the apparatus according to the invention.

In the figures, the same elements are denoted by the same reference numerals in each case. FIG. 1 shows a perspective view of an embodiment of the air sterilizer according to the invention from the right side. The air sterilizer comprises a housing 1. At one end of the housing 1 there is an air supply unit 5, in which a fan 3 is arranged in a fixed manner, which provides a flow of air in the apparatus. The fan 3 is protected from mechanical damage by a protective grille 11 located in the air supply unit 5 and ensures the inflow of air by the fan 3. The direction of the incoming air is indicated by an arrow in FIG. 1. On the air supply unit 5 control electronics 10 are arranged, to which the electrical wires 4 are connected. The housing 1 of the apparatus is sealed from the side by an end cover 20. A heat-insulated side cover 15 is attached to the end cover 20 in a fixed manner (e.g. by welding). It is fixed to the side cover by means of a cap 16 and its fixing screws 17. At the other end of the housing 1 of the apparatus an air outlet unit 6 is provided, which comprises an air filter 24. The air filter 24 is secured by a protective grille 11 that protects it from mechanical damage. The direction of the outgoing air is indicated by an arrow in FIG. 1. The housing 1 of the apparatus preferably has a carrier tab 12 and feet 13 which ensure the stability of the apparatus during operation. The electrical wires 4 provide electric power to the apparatus. The other electrical line 34 provides electric power to the electric heater 7.

Figure 2:
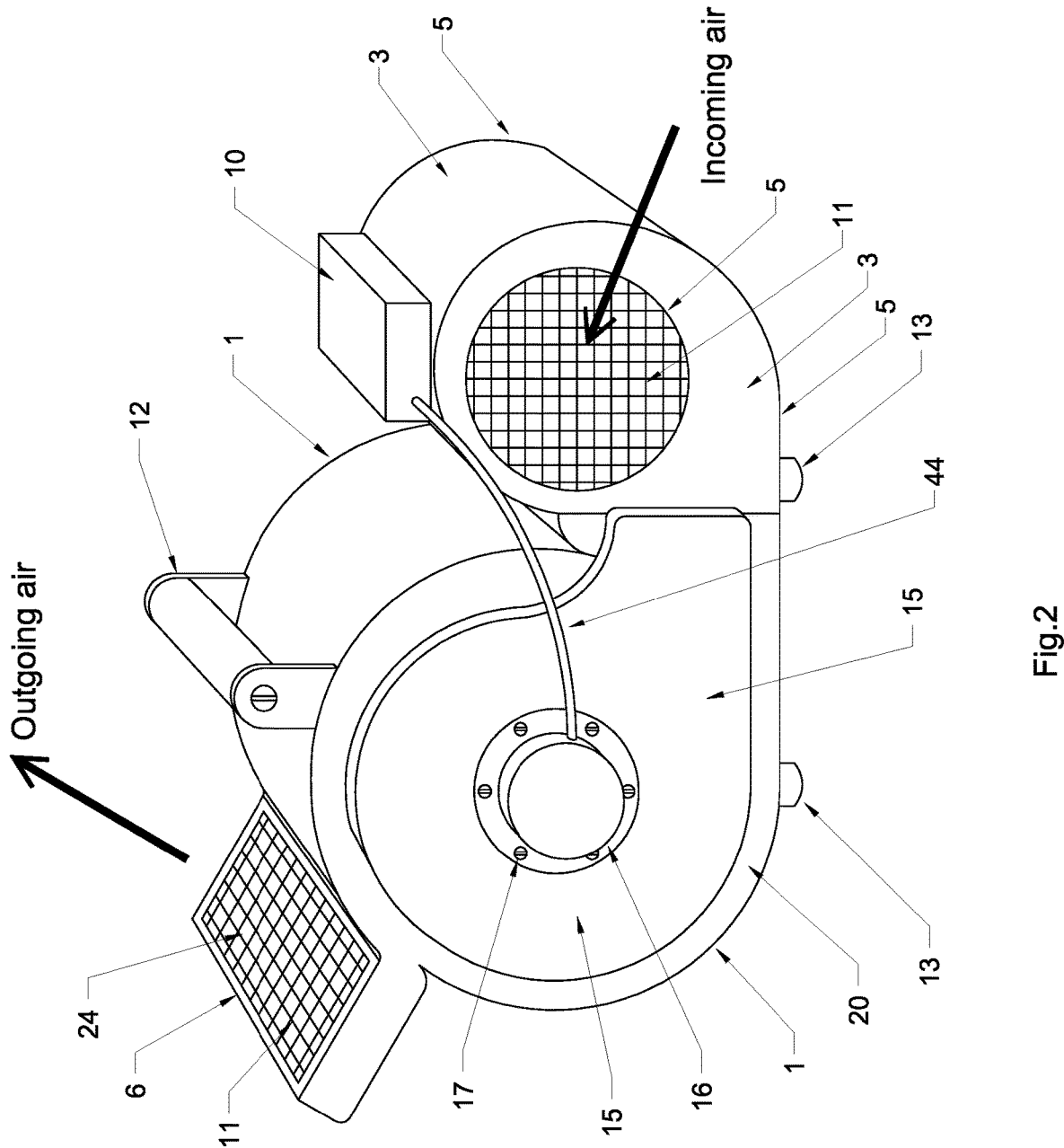
FIG. 2 shows a perspective view from the left of an embodiment of the apparatus according to the invention.

FIG. 2 shows a perspective view, from the left side, of the embodiment of the air sterilizer according to the invention shown in FIG. 1. The electric line 44 supplies electric power to the electric heater 7 and connects the temperature sensor 23 to the control electronics 10. The fan 3 is protected from mechanical damage by a protective grille 11 located in the air supply unit and ensures the inflow of air sucked in by the fan 3.

Figure 3:
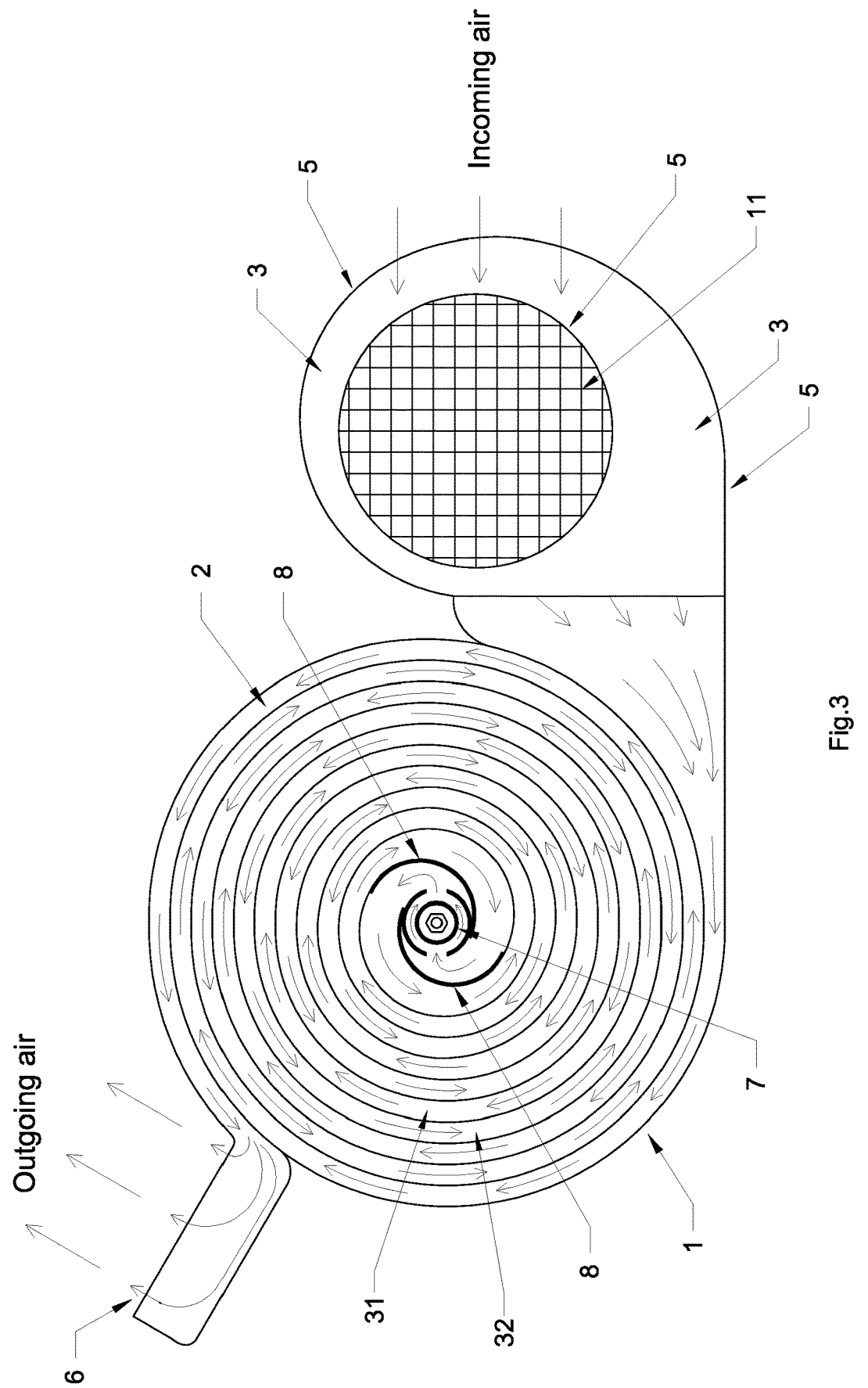
FIG. 3 shows an embodiment of the apparatus according to the invention in a schematic side view with the direction of air flow during operation.

FIG. 3 shows a schematic side view of an embodiment of an air sterilizer according to the invention, with the direction of air flow during operation, wherein the spiral plate heat exchanger 2 is shown within the housing 1 from the left side. The spiral plate heat exchanger 2 has an air inlet duct 31 running from the air inlet unit 5 to the electric heater 7 and a counterflow air outlet duct 32 running from the electric heater unit 7 to the air outlet unit 6, said ducts 31, 32 running helically next to each other. The electric heating unit 7 is located within a reinforced internal unit 8 (so-called reaction chamber) of the spiral plate heat exchanger 2. The direction of air flow is indicated by arrows. The air flow is moved by a fan 3 located in the air inlet unit 5 at one end of the housing 1 of the apparatus.

As shown in FIG. 3, the air enters the air inlet unit 5, passes through the air inlet duct 31 to the electric heating unit 7 arranged in the center of the apparatus, then flows outwards through the air outlet duct 32 in the direction indicated by the arrows, and finally the air flows out of the air outlet unit 6.

Figure 4:
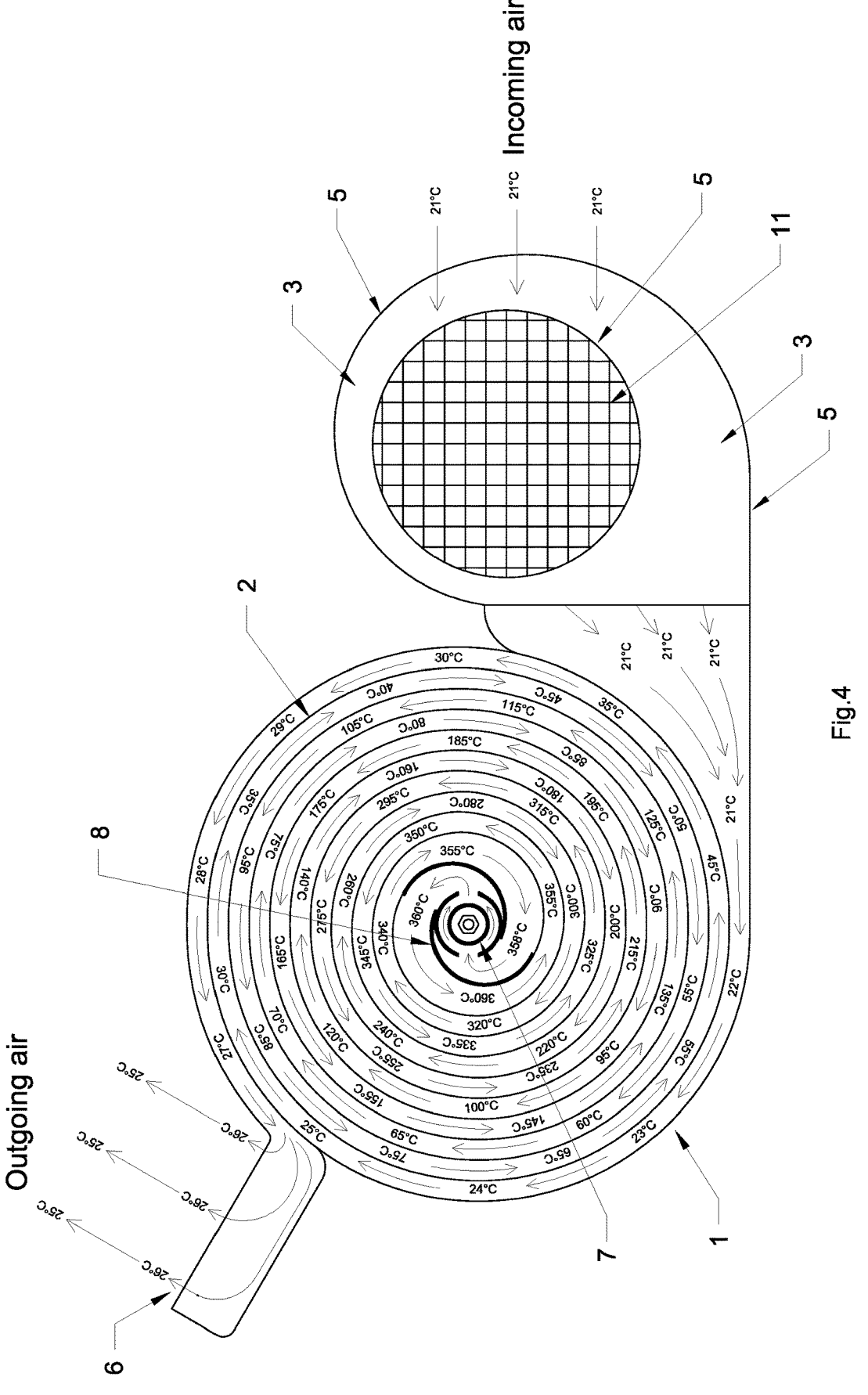
FIG. 4 shows an embodiment of the apparatus according to the invention, in a schematic side view with the direction of air flow during operation under operating temperature.

FIG. 4 shows an embodiment of an air sterilizer according to the invention in a schematic side view with the air flow direction during operation in a temperature range below 360° C. The housing 1 of the apparatus comprises the spiral plate heat exchanger 2, in the center of which the electric heating unit 7 is located. At one end of the housing 1 of the apparatus, a fan 3 is located in the air supply unit 5 in a fixed manner, which ensures the flow of air within the apparatus. The air flowing in through the air inlet unit 5 and then flowing through the spiral plate heat exchanger 2 exits from the apparatus through the air outlet unit 6. In FIG. 4, the air flow directions are indicated by arrows. The embodiment shown in the figure is based on an external ambient temperature of 21° C. The electric heating unit 7 heats the air moved in and out by the spiral plate heat exchanger 2 arranged within the reinforced internal unit 8 (reaction chamber) of the spiral plate heat exchanger 2 to an operating temperature of 360° C. FIG. 4 shows the approximate temperature distribution of the air flowing within the spiral plate heat exchanger 2. The temperature of the exhaust air blown out of the appliance is always higher than the temperature of the air sucked in by the fan 3. This is an important feature because it prevents the condensation of vapour from the air flowing in the air outlet duct 32 of the spiral plate heat exchanger 2 running from the electric heating unit 7 and in the air outlet unit 6.

Figures 5, 6:
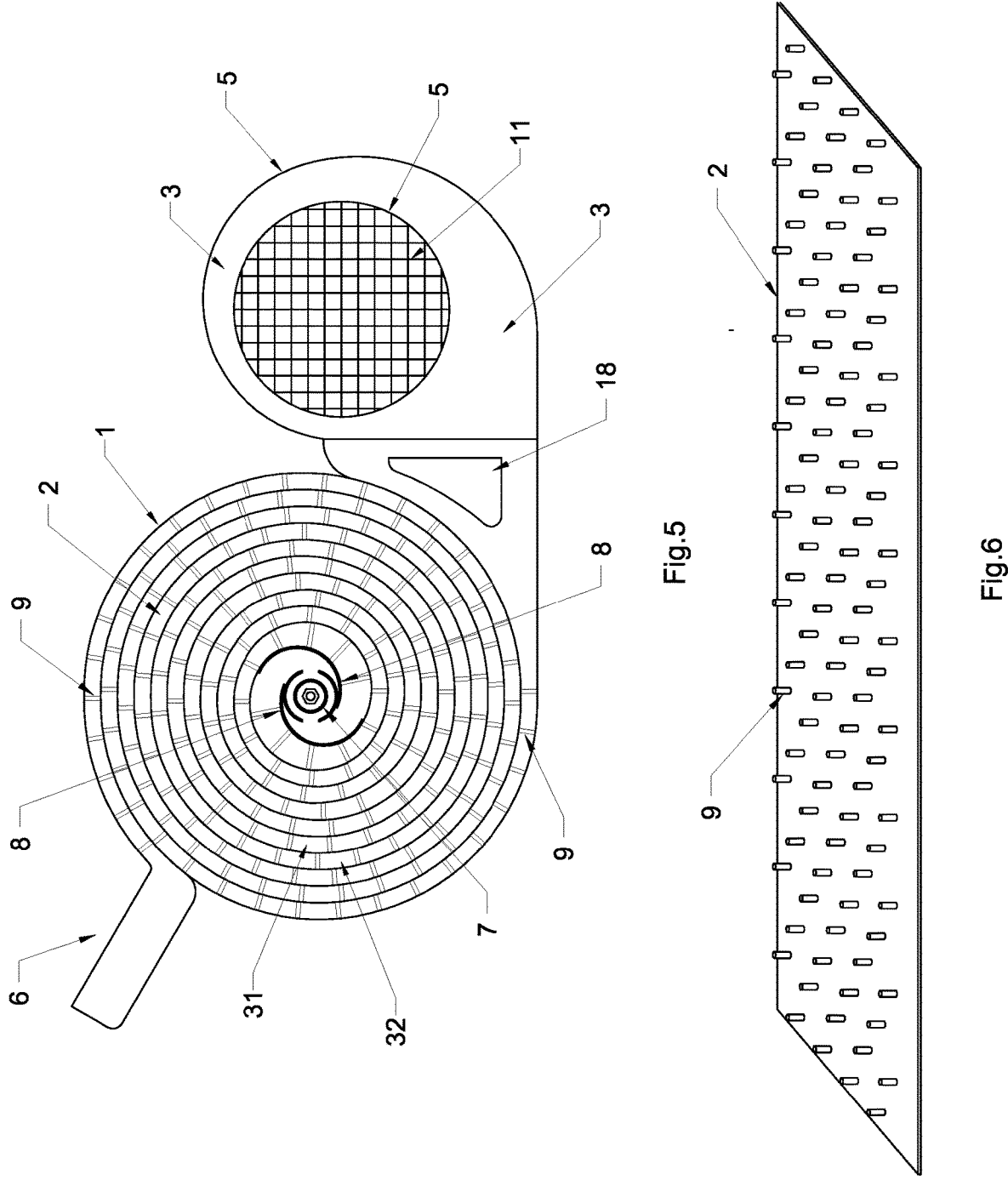
FIG. 5 shows an embodiment of the apparatus according to the invention, in a schematic side view with spacer pins.
FIG. 6 shows a schematic unfolded perspective view of the spiral plate heat exchanger with spacer pins, according to the invention.

FIG. 5 shows a schematic side view of an embodiment of the air sterilizer according to the invention. The spiral plate heat exchanger 2 is arranged in the housing 1 of the apparatus, wherein spacer pins 9 provide an even distance between the adjacent plates of the spiral plate heat exchanger 2. In this embodiment, the plates of the spiral plate heat exchanger 2 are bent from flat plates, and the spacer pins 9 of uniform height are permanently fixed (for example by welding) to one or both sides of the plates.

At the center of the housing 1 is the electric heating unit 7, which is surrounded by the reinforced internal unit 8 (reaction chamber) of the spiral plate heat exchanger 2, the temperature of which is between 310 and 600° C. during operation. At one end of the housing 1 of the apparatus, a fan 3 is arranged in the air inlet unit 5 in a fixed manner, which ensures the flow of air. Air enters the air inlet unit 5 and the air sucked in by the fan 3 exits the air outlet unit 6. The respective air outlets 18 are in flow communication with the air inlet units 5 on both sides of the fan 3, so that during operation the fan 3 not only blows air into the air inlet duct 31 of the spiral plate heat exchanger 2 but also blows air through the air outlets 18 on both sides of the apparatus. The air blown out of the air outlet 18 is returned to the air inlet 31, as it will be described in detail later.

FIG. 6 is a schematic unfolded perspective view of the spiral plate heat exchanger 2 of the air sterilizer according to the invention with the spacer pins 9. The spacer pins 9 provide an even gap between the plates of the spiral plate heat exchanger 2 in the air ducts and also have a heat exchanger role due to their thermal conductivity as they are typically made of metal.

Figures 7, 8:
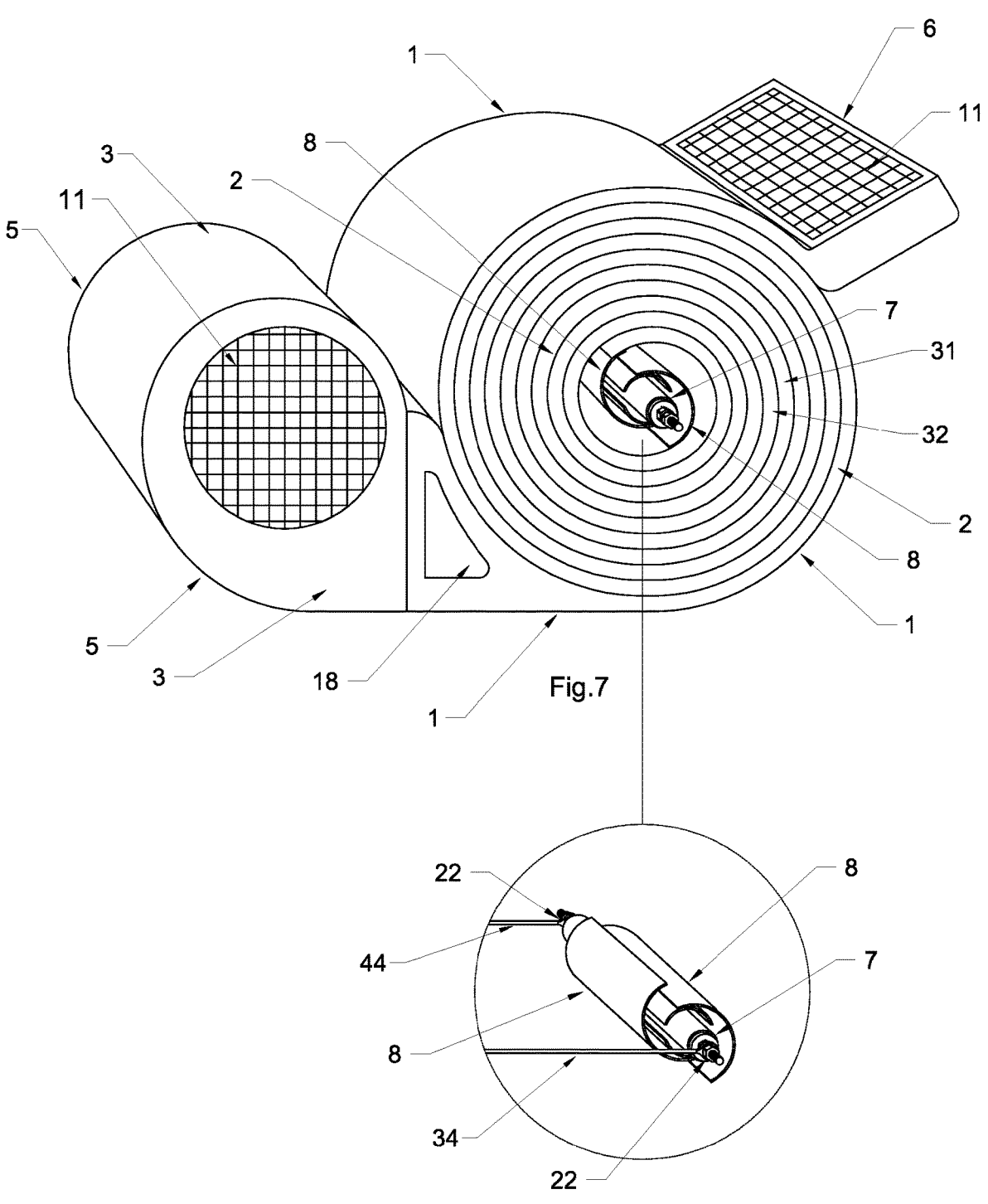
FIG. 7 shows an embodiment of the apparatus according to the invention on the right side, in a perspective view, without the end cover and the side cover.
FIG. 8 shows a perspective view, from the right side, of the electric heating unit and the internal reinforced unit (reaction chamber) of the spiral plate heat exchanger according to the invention.

FIG. 7 shows a perspective view of an embodiment of the air sterilizer according to the invention, without an end cover and a side cover on the right side. In the housing 1 of the apparatus there is a spiral plate heat exchanger 2, in the center of which there is an electric heating unit 7, which is surrounded by a reinforced internal unit 8 (reaction chamber) of the spiral plate heat exchanger 2, wherein during operation, the temperature is between 310-600° C. At one end of the housing 1 of the apparatus there is an air supply unit 5 with a fan 3 arranged in a fixed manner, which ensures the flow of air in the apparatus. The fan 3 is protected from mechanical damage by a protective grille 11. At the other end of the housing 1 of the apparatus are the air outlet unit 6 and the other protective grille 11. One of the two air outlets 18 is located on the side of the housing 1 of the apparatus.

FIG. 8 shows a perspective view, from the right side, of the electric heating unit 7 of the air sterilizer according to the invention and the inner reinforced unit 8 (reaction chamber) of the spiral plate heat exchanger 2, wherein electrical wires 4 providing electric power to the electric heater 7 are connected to the electric connection terminals 22 of the electric heater 7 by screws. The reinforced internal unit 8 (reaction chamber) of the spiral plate heat exchanger 2 surrounds the electric heating unit 7 and directs the incoming air and the outgoing air. The reinforced inner unit 8 (reaction chamber) of the spiral plate heat exchanger 2 ensures an even distribution of the heat energy (310-600° C.) produced by the electric heating unit 7, as well as the heat-resistant durability of the inner unit of the spiral plate heat exchanger 2. For higher performance, several electric heating units 7 can be used, which can preferably be arranged next to one another, in parallel or in a triangular or circular arrangement within the reinforced inner unit.

Figures 9, 10:
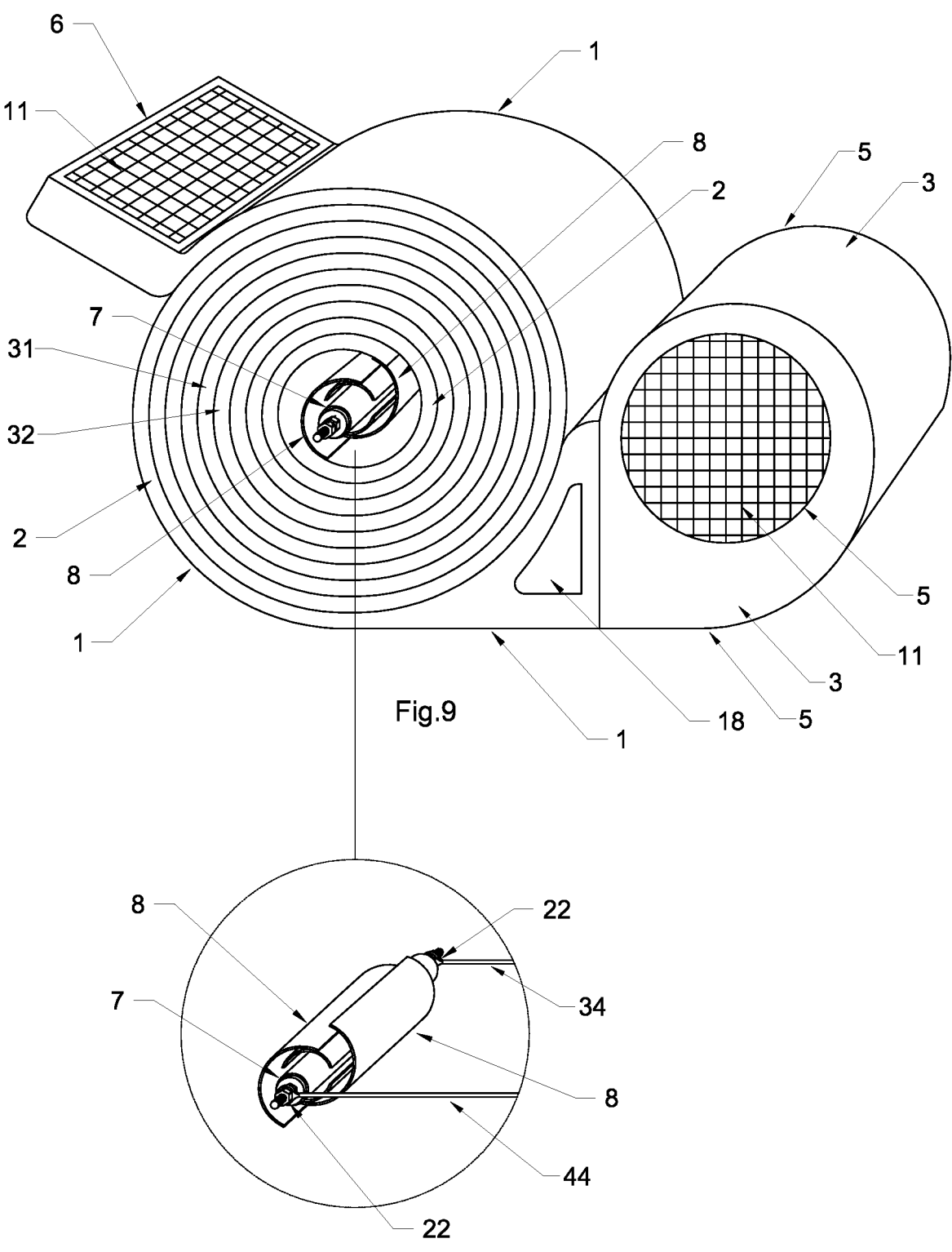
FIG. 9 shows an embodiment of the apparatus according to the invention, in a perspective view from the left side, without the end cover and side cover.
FIG. 10 is a perspective view, from the left side, an embodiment of the electric heating unit and the internal reinforced unit (reaction chamber) of the spiral plate heat exchanger according to the invention.

FIG. 9 shows a perspective view, from the left side, of the embodiment of the air sterilizer according to the invention shown in FIG. 7, without the end cover 20 and the heat-insulated side cover 15.

FIG. 10 shows a perspective view, from the left side, of an electric heating unit 7 of the air sterilizer according to the invention and an internal reinforced unit 8 (reaction chamber) of the spiral plate heat exchanger 2.

Figure 11:
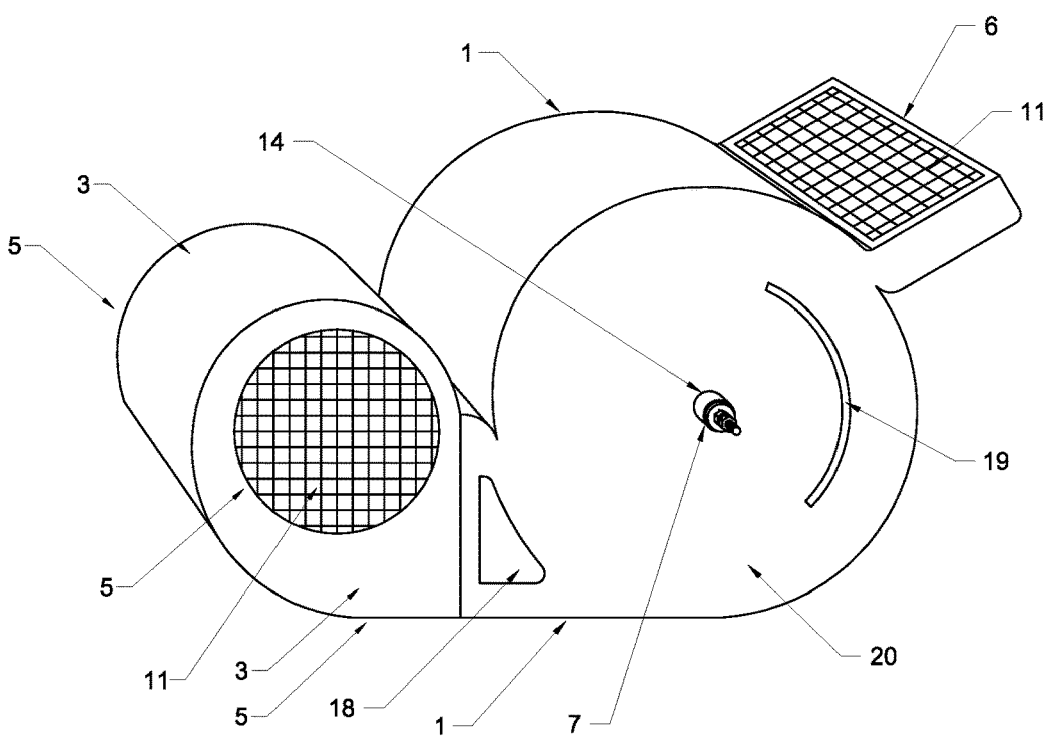
FIG. 11 shows an embodiment of the apparatus according to the invention, in a perspective view, from the right side, with an end cover but without the side cover.

FIG. 11 shows a perspective view, from the right side, of an embodiment of the air sterilizer according to the invention with the end cover 20, without the side covers. The side of the apparatus and the spiral plate heat exchanger 2 arranged therein are sealed on both sides by a respective end cover 20. An air inlet 19 is formed on each of the end covers 20 and is positioned to open into the air inlet duct 31 leading to the electric heating unit 7. A guide hole 14 for the electric heater 7 is further formed in the end cover 20, in which one end of the electric heater 7 is located. There is an air outlet 18 on each side of the housing 1 of the apparatus. It should be noted that although not shown in the drawings, the air inlet ducts 31 and the air outlet ducts 32 of the spiral plate heat exchanger 2 are also hermetically sealed from each other by the end cover 20.

Figure 12:
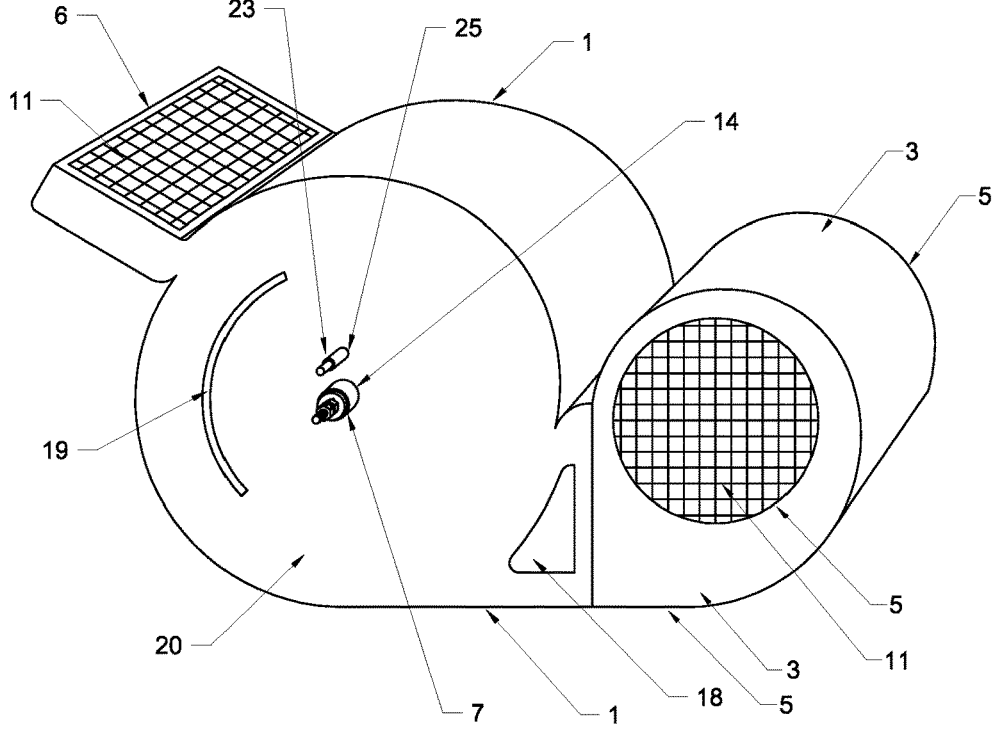
FIG. 12 shows an embodiment of the apparatus according to the invention, in a perspective view, from the left side, with the end cover but without the side cover.

FIG. 12 shows a perspective view, from the left side, of an embodiment of the air sterilizer according to the invention with the end cover 20 and without side covers. A guide hole 14 is also formed in the left-side end cover 20 for the electric heater 7, in which the other end of the electric heater 7 is accommodated. In addition, a guide hole 25 is formed in the left-side end cover 20 for the temperature sensor 23 in which the temperature sensor 23 is located.

Figure 13:
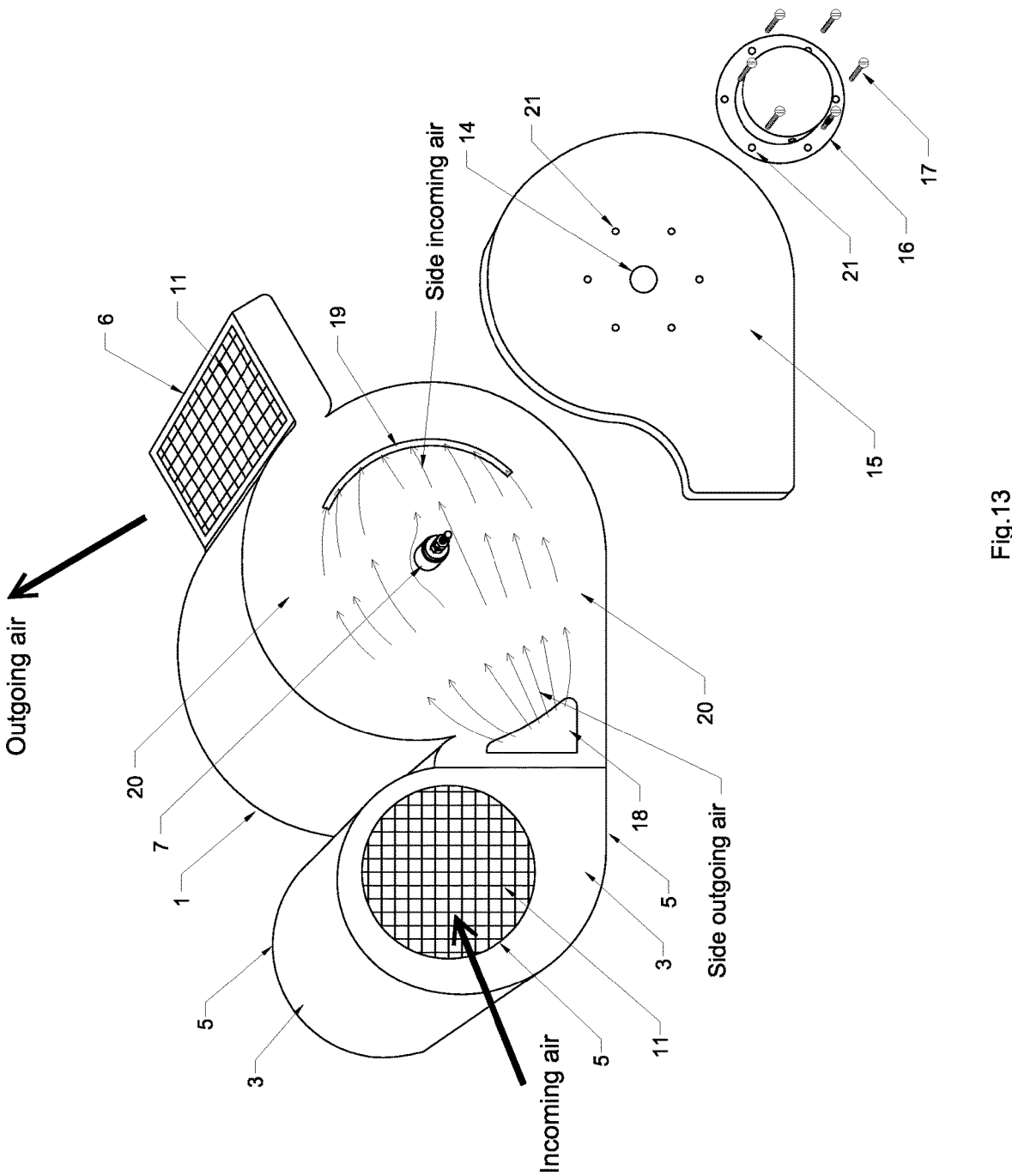
FIG. 13 shows an embodiment of the apparatus according to the invention, in a perspective view from the right side, with exploded parts, with the end cover and with the air flow directions during operation of the apparatus.

FIG. 13 shows a perspective view, from the right side, of an embodiment of the air sterilizer according to the invention, with the end cover 20 and with exploded parts during operation of the apparatus, also indicating the air flow directions. The side of the housing 1 and the open sides of the spiral plate heat exchanger 2 are hermetically sealed by the end cover 20 on which the air inlet 19 is formed. When the fan 3 is operating, the air flows into the air inlet unit 5 and a part of the air continues to flow into the spiral plate heat exchanger 2 into its air inlet duct 31 as shown in FIG. 3, then flowing out from the electric heating unit 7 through the air outlet duct 32 and exits into the environment through it. When the fan 3 is operated, the air sucked in by the apparatus also exits the air outlets 18 formed on both sides of the housing 1 and flows through the chamber 33 formed between the end cover 20 and the heat-insulated side cover 15 and returns to the air inlet 31 through the two lateral air inlets 19. The purpose of this external ventilation is to provide air cooling, by means of ambient air, for the end cover that becomes hot during operation. The air flowing through the chamber 33 also keeps the temperature of the outer side cover 15 relatively low, so that it cannot cause burns. Its further purpose is to return the heat energy generated on the sides of the spiral plate heat exchanger 2, thus also on the side covers 20, back to the system of the spiral plate heat exchanger 2.

Figure 14:
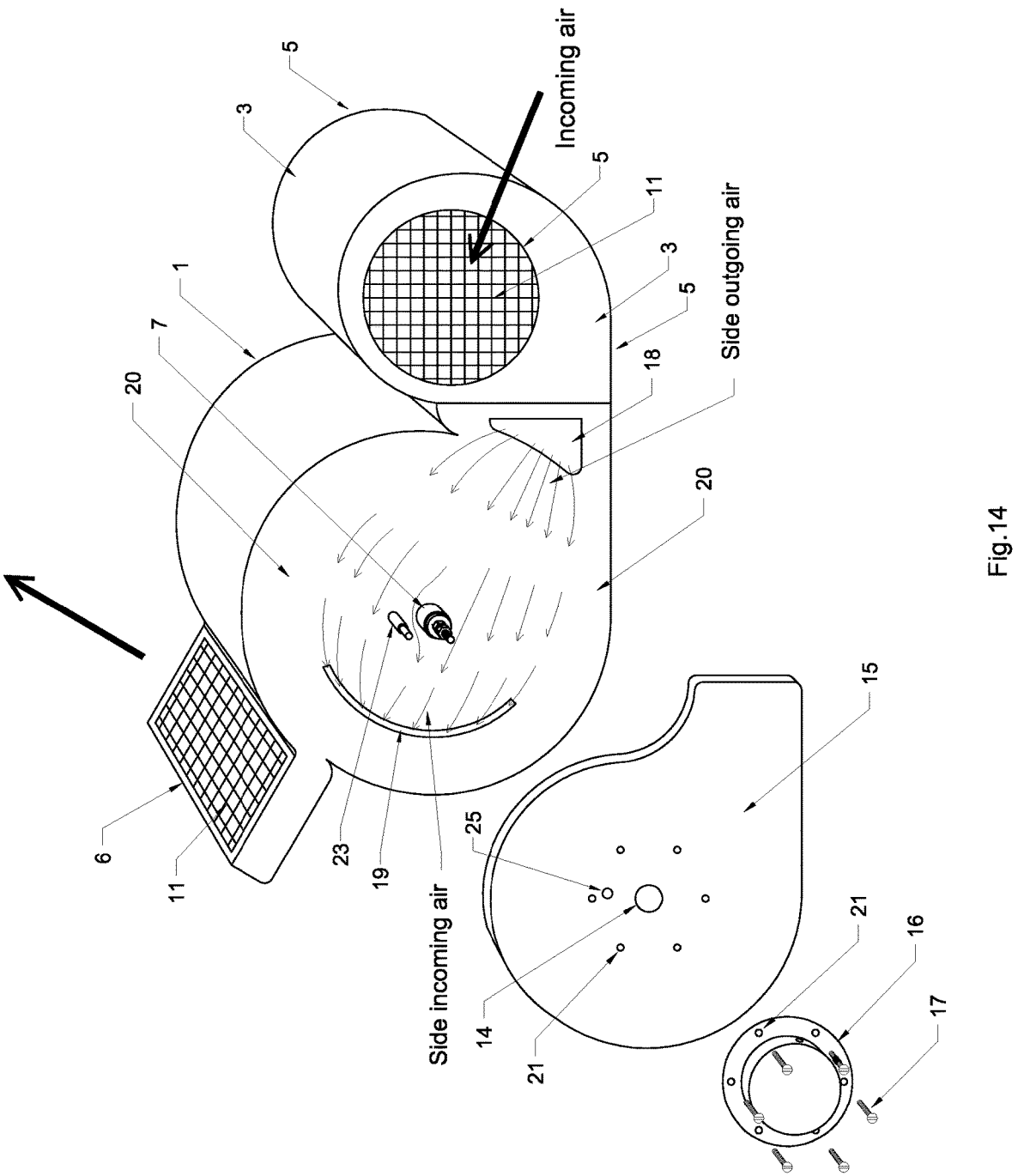
FIG. 14 shows a perspective view of the apparatus according to the invention, in a perspective view from the left side, with exploded parts, with the end cover and with the air flow directions during operation of the device.

FIG. 14 shows a perspective view, from the left side, of an embodiment of the air sterilizer according to the invention with the end cover 20, with exploded parts, also showing the direction of air flow during operation of the apparatus. A temperature sensor 23 is located in the guide hole 25 formed in the end cover 20, which extends into the space of the chamber 33 and is connected to the electrical line 44 shown in FIG. 2.

Figure 15:
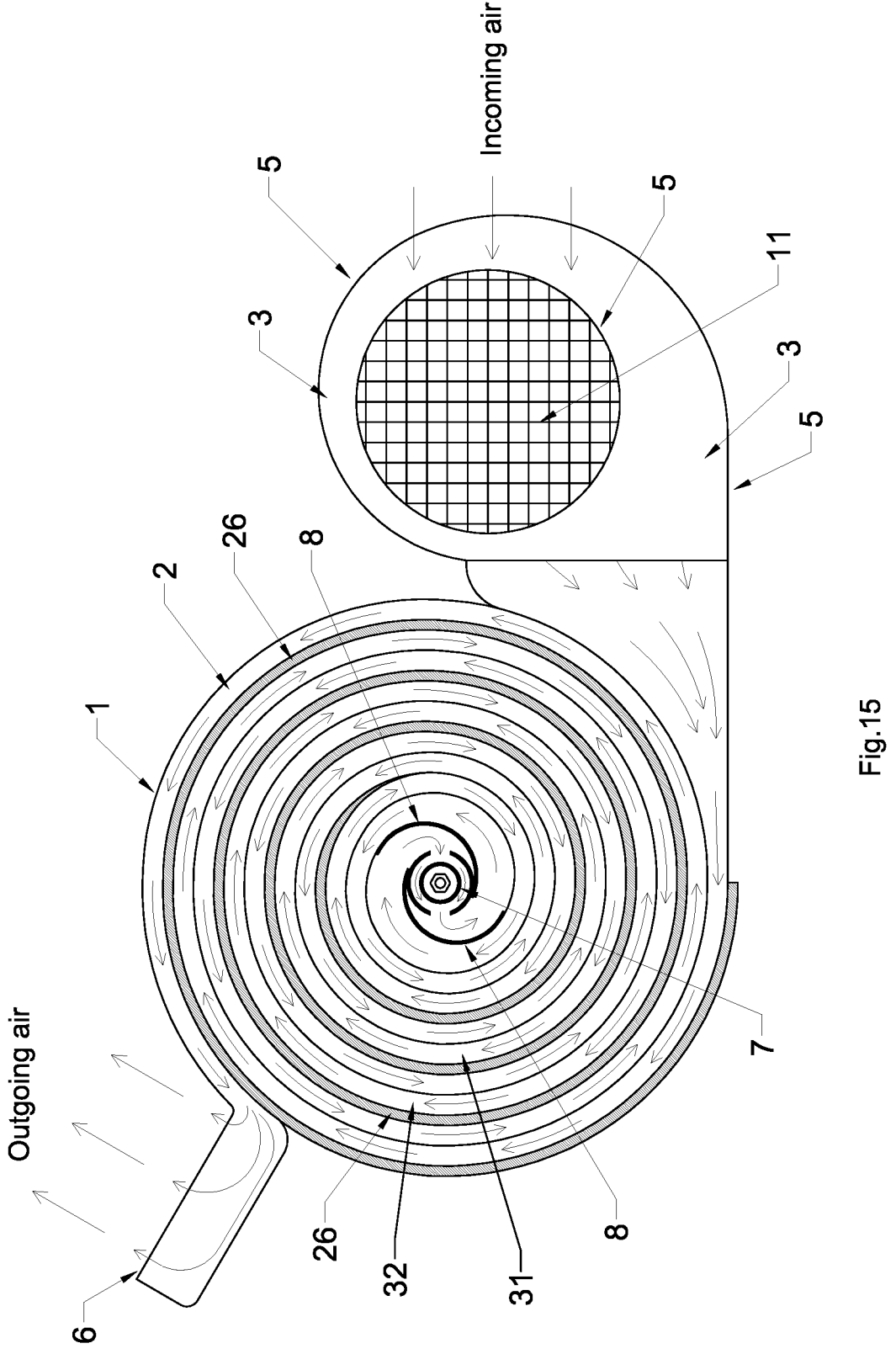
FIG. 15 shows a schematic side view of the apparatus according to the invention with a spiral plate heat exchanger having a heat-insulating duct in the direction of air flow during operation.
Figures 16, 17:
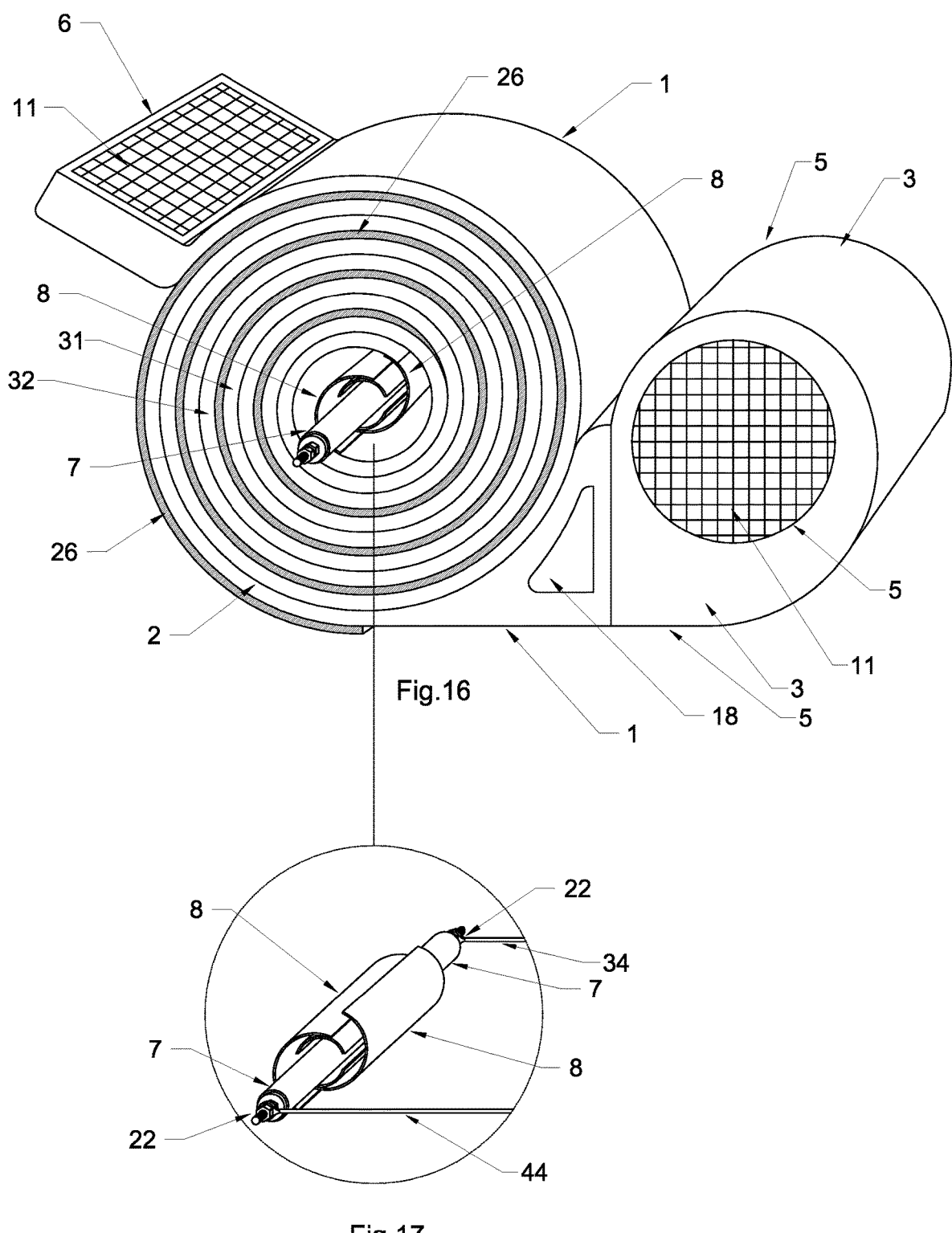
FIG. 16 shows a perspective view, from the left side, of the apparatus according to the invention, with a spiral plate heat exchanger with a heat-insulating duct, without the left-side end cover and the side cover.
FIG. 17 is a perspective view, from a left side, of an alternative embodiment of a longer electric heating unit and an internal reinforced unit (reaction chamber) of a spiral plate heat exchanger according to the invention.

FIG. 15 shows an embodiment of an air sterilizer according to the invention, in a schematic side view, with a spiral plate heat exchanger 2 provided with a heat-insulating channel 26, also showing the direction of the air flow during operation. In the housing 1 of the apparatus, the spiral plate heat exchanger 2 is shown in a side view, which has two counter-current channels, namely the air inlet duct 31 and the air outlet duct 32, which channels run helically next to each other, and wherein a spiral insulating channel 26 is arranged between the two ducts. Arrows indicate the direction of air flow, which is moved by a fan 3 located in an air inlet unit 5 located at one end of the housing 1 of the apparatus. As it can be seen in the drawings, the air enters the air inlet unit 5, travels along the path indicated by the arrows in the counter-current duct of the spiral plate heat exchanger 2 and flows out from the air outlet unit 6. The purpose of the heat insulating channel 26 is to reduce or prevent the transfer of heat from the inside to the outside perpendicular to the ducts. The heat insulating channel 26 is preferably a duct with a hollow interior, preferably filled with rock wool and hermetically sealed from its outer environment and from the air outlet duct 32 and the air inlet duct 31. FIG. 16 shows a perspective view, from the left side, of an embodiment of the air sterilizer according to the invention, without the end cover 20 and the heat-insulated side cover 15. FIG. 16 and the enlarged FIG. 17 show a perspective view, from the left side, of a longer electric heating unit 7 of the air sterilizer according to the invention and an embodiment of the internal reinforced unit 8 (reaction chamber) of a spiral plate heat exchanger 2 according to the invention, wherein the 4 electrical wires which provide the electric power supply are connected to the connection terminals by screws. The reinforced internal unit 8 (reaction chamber) of the spiral plate heat exchanger 2 surrounds the electric heating unit 7 and directs the air flowing inside the apparatus in the desired direction around the electric heating unit 7. The reinforced inner unit 8 (reaction chamber) of the spiral plate heat exchanger 2 ensures an even distribution of the heat (310-600° C.) produced by the electric heating unit 7 and also provides heat-resistant durability for the inner unit 8 of the spiral plate heat exchanger 2. This embodiment is essentially the same as the embodiment shown in FIG. 10, except that a longer electric heating unit 7 is used, the role of which is described in the following figures.

Figures 18, 19:
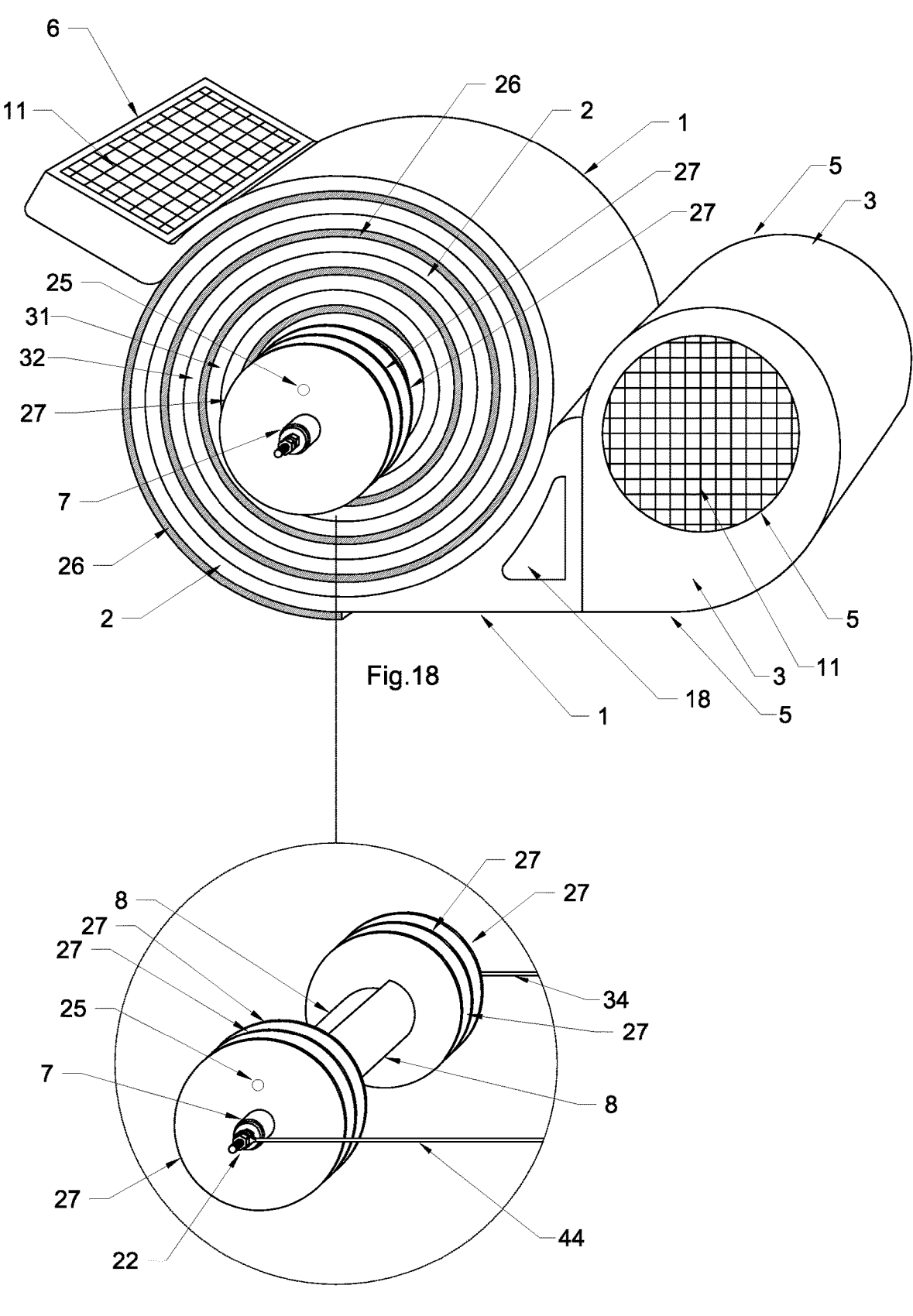
FIG. 18 shows a perspective view, from the left side, of the apparatus according to the invention, with a spiral plate heat exchanger having a heat-insulating channel and heat sinks on the electric heating unit, without the end cover and the side cover.
FIG. 19 shows a perspective view, from the left side, of a longer electric heating unit and an internal reinforced unit (reaction chamber) of the spiral plate heat exchanger with heat sinks according to the invention.

FIG. 18 shows a perspective view, from the left side, of an embodiment of the air sterilizer according to the invention, without the end cover 20 and the heat-insulated side cover 15. In the housing 1 of the apparatus there is a spiral plate heat exchanger 2 provided with a spiral thermal insulation channel 26, in the center of which there is an electric heating unit 7 which is longer than the embodiment shown in FIGS. 1 to 14. At the end portion of this heating unit 7, a plurality of heat releasing elements, for example the heat sinks shown in the drawings, are arranged. The purpose of the heat sinks 27 is to return the heat generated at the ends of the heating unit 7 and at the end cover 20, and thus also the heat flow, through the air inlet 19 up to the air inlet duct 31 running towards the heating unit 7. Thus, the lateral outward heat flow can be significantly reduced and heat loss through the side covers 15 can be minimized.

FIG. 19 shows a perspective view, from the left side, of the heat sinks 27 and the inner reinforced unit 8 (reaction chamber) of the spiral plate heat exchanger 2 located at the ends of the longer electric heating unit 7 of the air sterilizer according to the invention.

Figure 20:
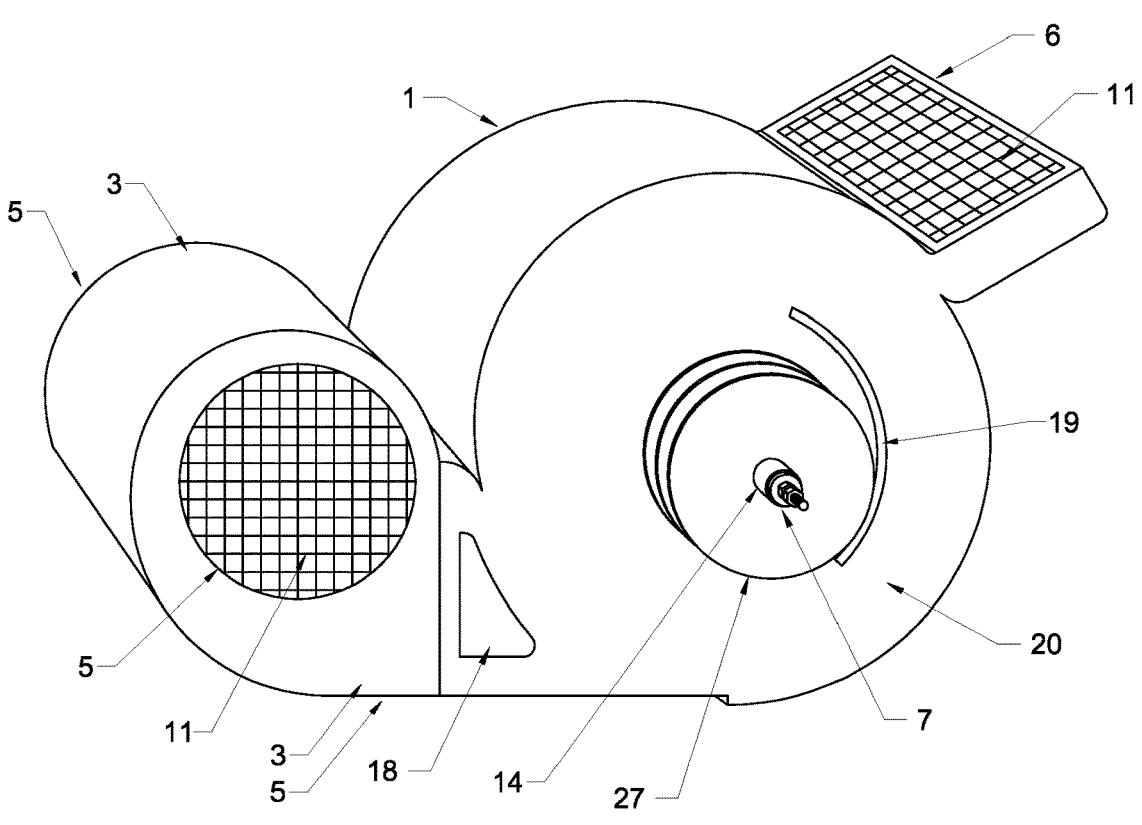
FIG. 20 shows an embodiment of the apparatus according to the invention, in a perspective view from the right side, with an end cover, without heat sinks and without side covers.

FIG. 20 shows a perspective view, from the right side, of an embodiment of the air sterilizer according to the invention, with the end cover 20, without the heat-insulated side cover 15. The side of the housing 1 of the apparatus and the sides of the heat insulating channel 26 and the spiral plate heat exchanger 2 accommodating therein are hermetically sealed by the end cover 20 on which the air inlet 19 is formed on both sides of the apparatus, said air inlets 19 always opening into the air inlet duct 31 running towards the electric heating unit 7. The guide hole 14 of the electric heater 7 is also formed on the end cover 20. In this guide hole 14 one end of a longer electric heater 7 is located, at the end of which heat sinks 27 are arranged. The two air outlets 18 are located on both sides of the housing 1 of the apparatus. At one end of the housing 1 of the apparatus there is an air supply unit 5 with a fan 3 arranged in a fixed manner, which ensures the flow of air in the apparatus and which is protected from mechanical damage by the protective grille 11. At the other end of the housing 1 of the apparatus are the air outlet unit 6 and the other protective grille 11. It should be noted that although it is not shown in the drawings, the side of the heat insulating channel 26 and the channels of the spiral plate heat exchanger 2 are also sealed laterally by the end cover 20.

Figure 21:
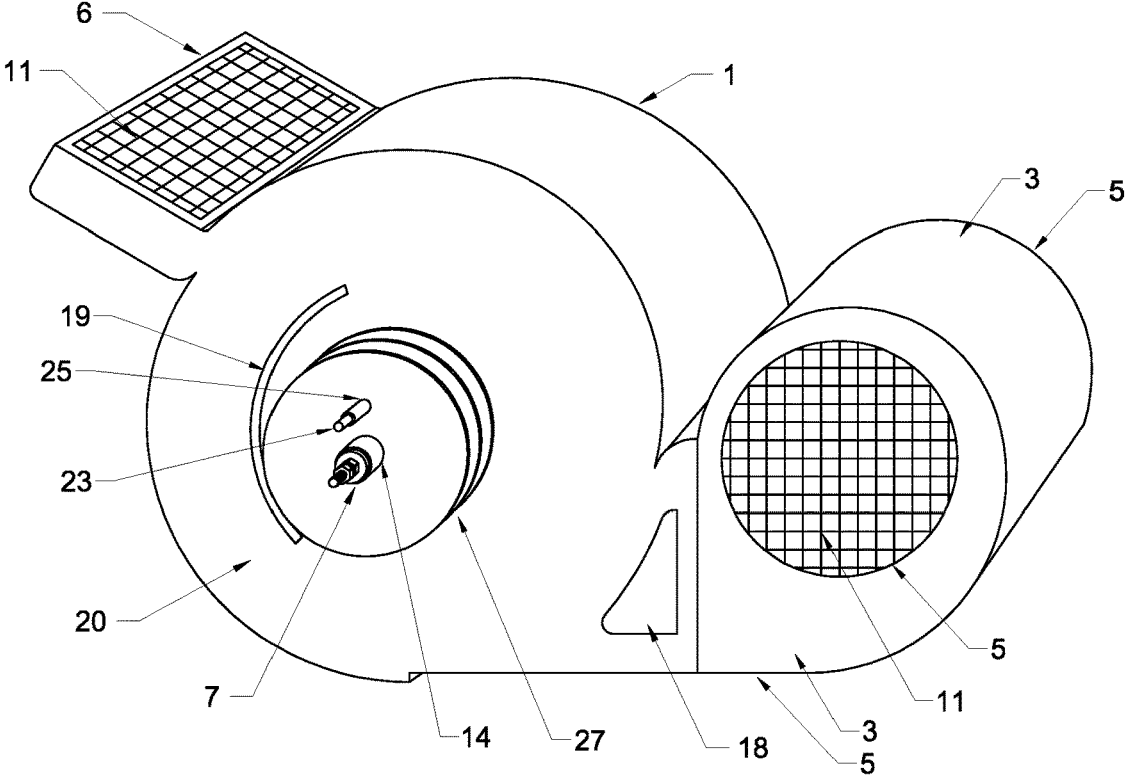
FIG. 21 shows an embodiment of the apparatus according to the invention, in a perspective view from the left side, with an end cover and with heat sinks, without side covers.

FIG. 21 shows a perspective view, from the left side, of an embodiment of the air sterilizer according to the invention, with the end cover 20, without the heat-insulated side cover 15. As shown in the figure, the guide hole 25 of the temperature sensor 23 is also guided through the heat sinks 27.

Figure 22:
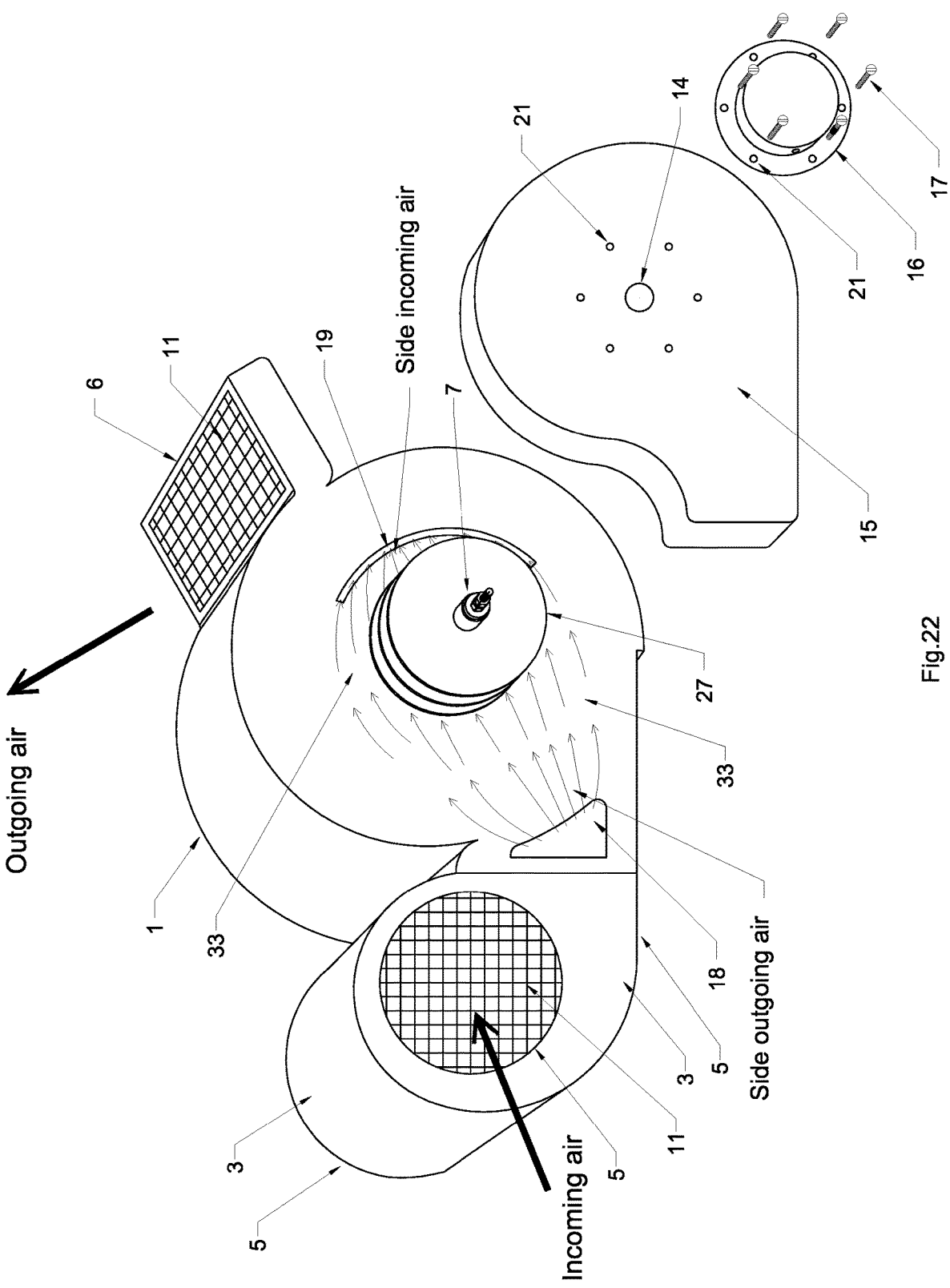
FIG. 22 shows an embodiment of the apparatus according to the invention, from a perspective view from the right side, with an end cover, heat sinks, exploded parts and with air flow directions during operation of the apparatus.

FIG. 22 shows a perspective view, from the right side, of an embodiment of the air sterilizer according to the invention, with the end cover 20 and with exploded parts, and showing the air flow directions during operation of the apparatus. The guide hole 14 of the electric heater 7 is further formed on the end cover 20, in which one end of an electric heater 7 of greater length is located, at the end of which the heat sinks 27 are arranged. In this embodiment, the depth of the thermally insulated side covers 15 is greater in order to accommodate the heat sinks 27 in the chamber 33. The dimensions of the chamber 33 are determined by the internal sizes of the side covers 15.

Figure 23:
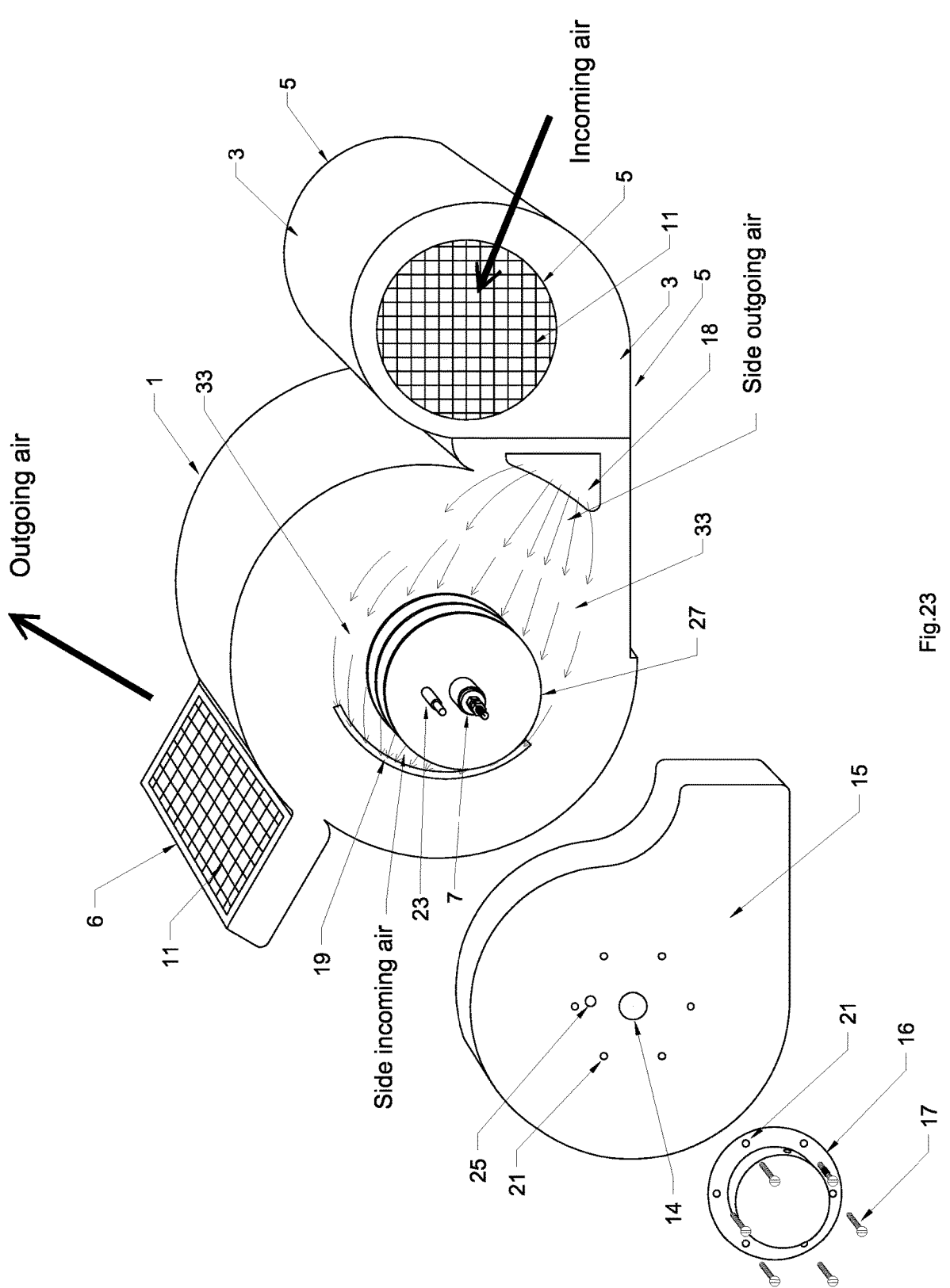
FIG. 23 shows an embodiment of the apparatus according to the invention, with a perspective view from the left side, with an end cover, heat sinks, exploded parts, and with the air flow directions during operation of the apparatus.

FIG. 23 shows a perspective view, from the left side, of an embodiment of the air sterilizer according to the invention, with the end cover 20 and with exploded parts, also showing the air flow directions during operation of the apparatus.

As described above, the apparatus according to the invention uses a spiral plate heat exchanger 2 which applies air cooling on both sides and wherein the heat-generating electric heating unit 7 can be accommodated in the inner central part of the spiral plate heat exchanger 2.

The purpose of the electric heating unit 7 is to heat the air flowing in the spiral plate heat exchanger 2 and its internal unit 8 (reaction chamber) to a temperature of 310-600° C., whereby the viruses in the incoming air are immediately destroyed by the high temperature. During operation of the apparatus, the air flowing in the reinforced internal unit 8 (reaction chamber) of the spiral plate heat exchanger 2 and in the central part of the spiral plate heat exchanger 2 has approximately a constant operating temperature along a section of at least 60-100 cm, so the viruses in the air are subject to the heat for longer time to achieve perfect virus removal. If, for example, a fan 3 with a power of 120 Watts is used, the air flow rate in the innermost section of the ducts 31, 32 of the spiral plate heat exchanger 2 is ca. 5 m/s, as a result of which the viruses and other pathogens transported by the air flowing within the apparatus remain in the innermost section of at least 100 cm of the ducts 31, 32 for ca. 0.2 second, which is sufficient at said temperature to kill almost 100% of the viruses and other pathogens. (The prescribed operating parameters for indoor heat sterilization in healthcare are: 45 minutes at 160° C., 25 minutes at 180° C., 10 minutes at 200° C. to ensure complete sterility of medical devices. Based on these data, a temperature of 320° C. is required for 0.1 second to achieve complete sterility). Reference:

https://semmelweis.hu/nepegeszsegtan/files/2019/03/
1819_II_AOKgy02_Sterilizálás.pdf FIG. 4 shows the temperature distribution inside the apparatus at an operating temperature of 360° C. Due to the design of the apparatus, the resulting high temperature inside the apparatus is concentrated in the reinforced internal unit 8 (reaction chamber) of the spiral plate heat exchanger 2, which is important because the heat generated therein can better managed, there is enough space and time to cool it back efficiently in a way that the generated heat energy is returned into the system through the spiral plate heat exchanger 2 and reused. In addition to the air sterilization, another practical aspect is the practical applicability of the apparatus. One of the basic conditions for this is that the outer covers of the apparatus do not become too hot during operation. To this end, the heat must be kept inside the apparatus, which can be used again in the thermal energy system of the apparatus. With the right dimensioning and design, perfect air sterilization and outstanding energy-saving operation can be achieved and the outer covers of the apparatus do not heat up. The air inlet duct 31 running from the air supply unit 5 to the electric heater unit 7 and the counterflow air outlet duct 32 running from the electric heater unit 7 to the air outlet unit 6 run helically next to each other so that the incoming air can receive the heat energy of the outgoing air without getting into contact with each other, thus allowing the outgoing air to cool back sufficiently. However, the sides of the spiral plate heat exchanger 2, especially around the sides of the reinforced inner unit 8 (reaction chamber) of the spiral plate heat exchanger 2 and at the ends of the electric heater 7, have very high temperature during operation, so double-sided air cooling is of key importance from the point of view of practical applicability.

The fan 3 is preferably a radial fan, such as the radial fan TS400 SIROCO of SIROCO CLEYENS NP GROUP. The spacer pins 9 provide an even gap between the plates of the spiral plate heat exchanger 2 during its manufacture and thereafter in order to maintain a corresponding even gap, and the spacer pins 9 also have a role of heat exchange due to their thermal conductivity.

For an even more sophisticated operation of the apparatus, the spiral plate heat exchanger 2 (FIG. 15) is provided with a heat-insulating channel 26 in order to reduce or prevent the outward heat flow perpendicular to the ducts. Furthermore, a longer electric heater 7 is provided at the ends of electric heaters 7 (FIGS. 18 and 19). In this case, in the chamber 33, the heat sinks 27 dissipate the generated heat from the ends of the electric heating unit 7 and provide laminar air flow and heat dissipation for the double-sided air cooling, which provides an outstanding thermal insulation effect on the sides of the apparatus. Additionally, the heat sinks 27 also direct the generated heat energy into the air inlet duct 31 through the air inlets 19 arranged on both sides of the apparatus. Using this technology, premium quality energy consumption can be achieved in the apparatus without outer covers' heating up.

The control electronics 10 allows to regulate the internal operating temperature by means of the temperature sensor 23. The housing 1 of the apparatus is preferably provided with 12 carrying tabs for moving the apparatus and feet 13 for stable placement.

The apparatus is preferably designed to be capable of operating at both 6-48 V DC and 110-230 V AC.

Upon demand, the apparatus may be equipped with a pollen filter, which can be placed in the air outlet unit 6, which is fixed by the protective grille 11, and filters out the virus-free air flowing out so that patients suffering from allergy can also use it without risk.

Furthermore, the apparatus can also be used for room heating by reducing the power of the spiral plate heat exchangers 2, while the sterilization of the intake air remains unchanged.

Instead of the control electronics 10, a simple bimetallic thermal switch can be used to regulate the internal temperature, and instead of the temperature sensor 23, a bimetallic thermometer can be built in to measure the internal temperature.

The specific embodiments described herein are only for illustrative purposes, and it will be apparent to those skilled in the art how the embodiments shown may be modified or combined with one another to provide additional embodiments within the scope of the invention.

The air sterilizer according to the invention can be used continuously in the immediate environment of humans and living beings without risking their health. The apparatus sucks in the air infected with coronavirus from its surroundings and then immediately destroys the Covid 19 coronavirus contained in the intake air inside the reaction chamber at a temperature of 310-600° C. It blows the cleaned hot air back into its environment by cooling it down (approximately to the temperature of the intake air). The apparatus has been developed for everyday home use, therefore it is structurally designed so that despite its high internal operating temperature, its external components and covers do not warm up and the temperature of the cleaned air blown out is almost the same as the temperature of the intake air. By using the apparatus continuously, virus-free healthy air can be provided in a room or in the environment.

The antiviral air sterilization apparatus according to the invention can be preferably used in particular in areas where several persons are present in a closed space and the concentration of viruses in the air is therefore increased. Such areas in healthcare include hospitals, corridors and waiting areas, as well as aircraft cabins, airports, ambulances, taxis, public transport, other closed-space passenger transport tools (e.g. elevators, cable cars, etc.). It can also be used in law enforcement organizations, shops, theatres, homes, and any area where there is a risk of virus infection.

The apparatus according to the invention can also be used effectively in agriculture and animal husbandry, since trans-infections from various viruses and bacteria (e.g. avian influenza, swine fever, sterilization) are a serious problem for animals kept indoors, which can cause amazing damage to livestock. The apparatus can be used to drastically reduce or eliminate trans-infections and to effectively localize infections.

A further advantage of the air sterilizer according to the invention is that, due to its simple structural design, it can be manufactured cost-effectively and in an environmentally conscious manner, in a variety of shapes and performances. It can also be used effectively in a smaller form with a battery power supply of 12-48 V DC, for everyday use, even as personal protective equipment. It may be widely used due to its favourable commercial price.

The invention claimed is:

1. An air sterilizer comprising
   a housing having, at one end thereof, an air supply unit in which a fan is arranged in a fixed manner,
   a spiral plate heat exchanger arranged in the housing and comprising an electric heating unit in its central part,
   an air outlet unit at the other end of the housing,
   wherein the spiral plate heat exchanger has an air inlet duct running from the air inlet unit to the electric heater and a counterflow air outlet duct running from the electric heater to the air outlet unit, which ducts run helically next to each other;

wherein
   an air outlet is formed at one end of the housing, adjacent to the air supply unit, on each side of the housing,
   each side of the spiral plate heat exchanger is sealed by an end cover,
   an air inlet is formed on the end covers, which opens into the air inlet duct running to the electric heating unit,
   a guide hole is formed in one of the end covers for a temperature sensor, wherein a temperature sensor is accommodated in said end cover,
   in the spiral plate heat exchanger there is a constant distance between the adjacent plates of the air inlet duct and the air outlet duct,
   on the end covers there is a heat-insulated side cover on both sides of the air sterilizer, said side covers being sealed to the housing and defining a chamber which establishes flow communication between the air outlet and the air inlet on the same side of the air sterilizer.

2. The air sterilizer according to claim 1, characterized in that the spiral plate heat exchanger has a reinforced inner unit for holding the electric heating unit, said reinforced inner unit being made of steel or stainless steel or aluminium.

3. The air sterilizer according to claim 1, characterized in that the plates of the spiral plate heat exchanger are made of aluminium, copper, steel or stainless steel.

4. The air sterilizer according to claim 1, characterized in that an air filter is arranged in the air outlet unit.

5. The air sterilizer according to claim 1, characterized in that the plates of the spiral plate heat exchanger are bent from a flat plate and a plurality of spacer pins are arranged between the plates.

6. The air sterilizer according to claim 5, characterized in that the spacer pins are made of aluminium, copper, steel or stainless steel.

7. The air sterilizer according to claim 1, characterized in that the plates of the spiral plate heat exchanger are bent from a plate with pressed protrusions of constant height, the protrusions serving as spacers between adjacent plates.

8. The air sterilizer according to claim 1, characterized in that a heat-insulating channel is arranged between the adjacent air inlet ducts and air outlet ducts.

9. The air sterilizer according to claim 1, characterized in that heat-dissipating elements are arranged at the ends of the electric heating unit, within the lateral chambers.

10. The air sterilizer according to claim 8, characterized in that the heat-insulating channel is a hollow duct filled with rock wool and hermetically sealed from the outside environment, the air outlet duct and the air inlet duct.

* * * * *